(12) United States Patent
Zeng et al.

(10) Patent No.: US 8,578,797 B2
(45) Date of Patent: Nov. 12, 2013

(54) MULTI-SECTION SEDIMENT PORE WATER SAMPLER

(75) Inventors: Eddy Y. Zeng, Guangzhou (CN); Shiping Xu, Guangzhou (CN); Lianjun Bao, Guangzhou (CN)

(73) Assignee: Guangzhou Institute of Geochemistry Chinese Academy of Sciences, Guangzhou, Guangdong (CN)

( * ) Notice: Subject to any disclaimer, the term of this patent is extended or adjusted under 35 U.S.C. 154(b) by 91 days.

(21) Appl. No.: 13/144,080

(22) PCT Filed: Jan. 29, 2011

(86) PCT No.: PCT/CN2011/070789
§ 371 (c)(1),
(2), (4) Date: Jul. 11, 2011

(87) PCT Pub. No.: WO2012/097528
PCT Pub. Date: Jul. 26, 2012

(65) Prior Publication Data
US 2012/0180578 A1   Jul. 19, 2012

(51) Int. Cl.
*G01N 1/10* (2006.01)
(52) U.S. Cl.
USPC ..................... 73/863.23; 73/864.74
(58) Field of Classification Search
None
See application file for complete search history.

(56) References Cited

U.S. PATENT DOCUMENTS

| 3,080,760 | A | * | 3/1963 | Piersma ..................... 73/863.31 |
| 3,218,869 | A | * | 11/1965 | Fields et al. ................ 73/863.31 |
| 3,596,719 | A | * | 8/1971 | Koziski ........................... 175/20 |
| 4,335,622 | A | * | 6/1982 | Bartz .......................... 73/864.74 |
| 5,062,309 | A | * | 11/1991 | Voll et al. ................... 73/864.44 |
| 5,922,975 | A | * | 7/1999 | Butler et al. ................ 73/864.74 |
| 7,430,929 | B1 | * | 10/2008 | Vroblesky ................. 73/863.23 |
| 8,051,727 | B1 | * | 11/2011 | Murphy et al. ............ 73/864.74 |
| 2012/0016264 | A1 | * | 1/2012 | Weidenhamer et al. ...... 600/576 |

* cited by examiner

*Primary Examiner* — Robert R Raevis
(74) *Attorney, Agent, or Firm* — Loginov & Associates, PLLC; William A. Loginov

(57) ABSTRACT

The present invention discloses a multi-section sediment pore water sampler, which comprises a plurality of sampling units arranged coaxially and separated with each other; this arrangement ensures no water exchange occurred between two adjacent sampling units, collection of the sediment pore water samples from different depths of a same position is realized, whereby to facilitate organic pollutant sampling in sediment pore water at different depths according to different time resolutions. Furthermore, as the heights of the sampling units as well as the clearances between two neighboring sampling units may be various, in use users can configure the sampler according to the actual condition of the time resolution required, thus this sampler can also help improve the time resolution of water sampling.

17 Claims, 3 Drawing Sheets

MULTI-SECTION SEDIMENT PORE WATER SAMPLER

FIELD OF THE INVENTION

The present invention relates to a water sampler, and more particularly to a multi-section sediment pore water sampler.

BACKGROUND OF THE INVENTION

Persistent organic pollutants (POPs) refer to the highly toxic and hydrophobic organic compounds left and migrated in the environment and bio-accumulated in human and animal tissue. POPs in the environment mainly occur in the organic phase of sediment, having higher concentrations in pore water (water filling the spaces between grains of sediment). The hydrophobic organic compounds dissolved in natural water, including the water located in sediment pores, are cycled in ecosystems through evaporation, dissolution, adsorption and biological absorption processes. As the hydrophobic organic compounds have potential significant impacts on human health and the environment, it is important to accurately evaluate the density and biological effectiveness of the hydrophobic organic compounds dissolved in water, thus as a major carrier the sediment pore water sampling is necessary and important for water quality supervision against the persistent and hydrophobic organic pollutants.

Approaches for water sampling can be divided into two groups: passive and active approaches. As one of the most common active approaches, centrifugation may lead to the analysis results on the high side as its samples isolated by possibly excessive centrifugal speeds contain the pollutants dissolved in the inner water of the sediment particles. On the contrary, the passive approaches collect high-distribution-coefficient extraction medium rich samples; no additional power is required, thus applicable for uses in wild environment monitoring. The existing passive sediment pore water sampling mainly include two types of approaches: in-situ solid-phase micro-extraction and low-density polyethylene membrane extraction.

The in-situ solid phase micro-extraction instruments use high polymer coatings as adsorption medium, protecting the micro-extraction membranes as well as filtering out particles through using porous copper tubes and glass fiber membranes, however the adsorption membrane used herein are relatively expensive and easy to get damaged as well, because of this, it is inapplicable in field uses. The low density polyethylene membrane micro-extraction techniques use polyethylene membranes as adsorption medium, as in use the adsorption membranes are in direct contact with sediments, the particles adhered to the membranes may interference the determination results.

The abovementioned two types of water sampling approaches even have a drawback in common, which is difficult to collect water samples from different depths of a same position, and thus the water sampled cannot reflect the concentration changes over time.

SUMMARY OF THE INVENTION

In order to solve abovementioned problems, the present invention provides a multi-section sediment pore water sampler capable to collect water samples from different depths at a same position.

The multi-section sediment pore water sampler disclosed by the present invention comprises a plurality of sampling units arranged along the axis thereof in a straight line and separated with each other; the heights of the sampling units as well as the clearances between two adjacent sampling units may be various.

Furthermore, the sampling units are mounted in order on a main spindle which has, on one end thereof a pyramid with a stopping tray thereon, on the middle thereof a shaft, and on the other end thereof a threaded rod; the sampler further comprises a ring and a locking nut mounted on the threaded rod.

As another aspect of the present invention, each sampling unit comprises a center ring, which is sheathed by an adsorption film, a filtering membrane and a porous protection pipe from inside to outside, the center ring is provided with a separation tray, a pipe protection tray, a column, a positioning groove on the side of the separation tray, a positioning ring on the opposite side matched with the positioning groove, and a nozzle therein.

In another aspect of the present invention, the pyramid is a square pyramid.

The advantages of the present invention are as follows:

The multi-section sediment pore water sampler disclosed by the present invention has a plurality of sampling units arranged coaxially in a straight line and separated with each other, within this arrangement no water exchange is permitted between two adjacent sampling units. The sampler enables water sampling at different depths at the same position and so that the samples collected by different sampling units can reflect the historical pollution data for a position. Furthermore, as the heights of the sampling units as well as the clearances between two neighboring sampling units may be various, in use users can configure the sampler according to the actual condition of the time resolution required, thus this sampler can also help improve the time resolution of water sampling.

BRIEF DESCRIPTION OF THE DRAWINGS

The subject matter will become more clearly understood in light of the ensuing description of embodiments herein, with reference to the accompanying drawings, wherein.

DETAILED DESCRIPTION

Figure 1:
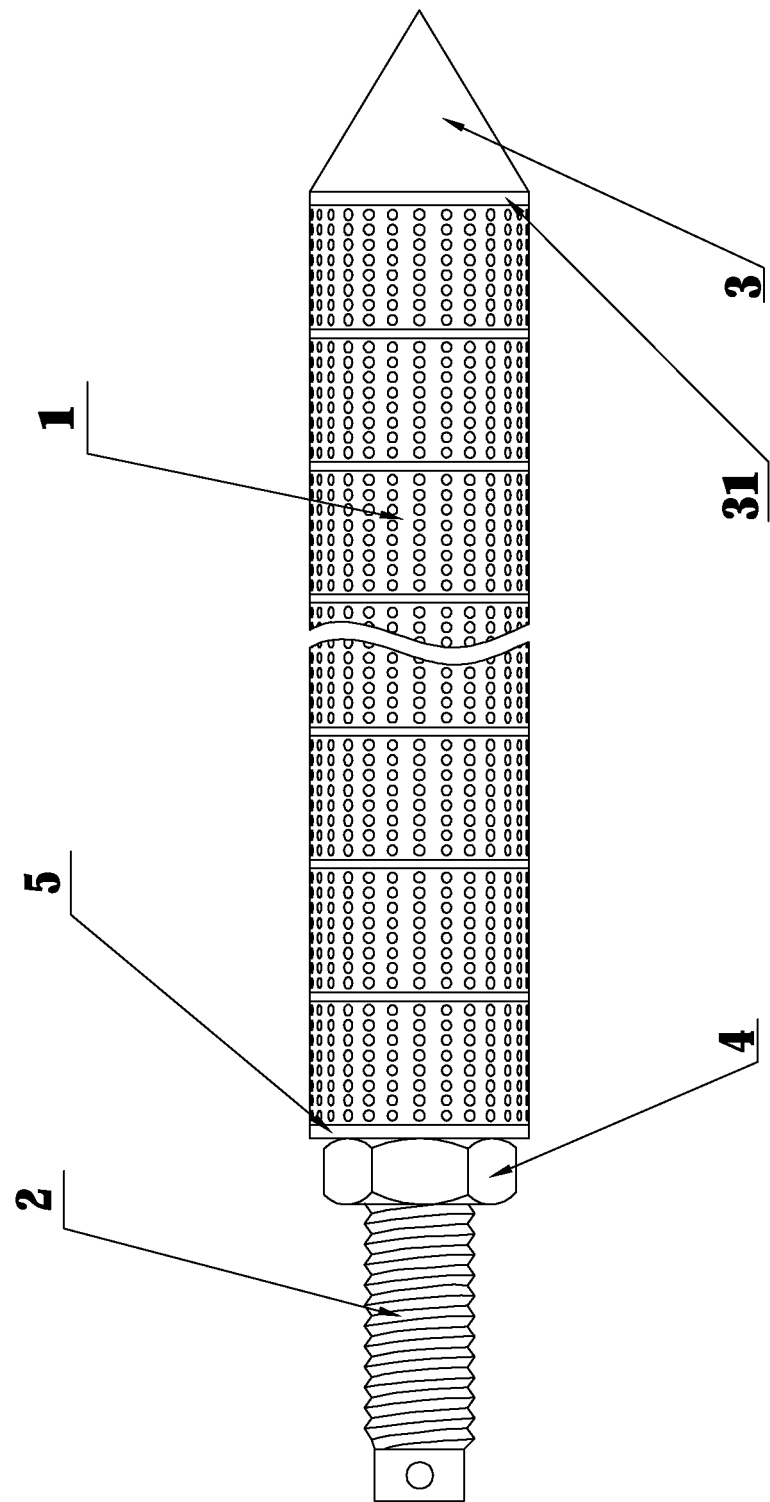
FIG. 1 is a schematic view of a sampler according to the present invention.

As shown by FIG. 1, the multi-section sediment pore water sampler disclosed by the present invention comprises several sampler units 1 arranged along the axis thereof in a straight line, the sampler units 1 are fixed coaxially and separated with each other, the heights of the sampling units 1 as well as the clearances between two neighboring sampling units 1 may be various.

From above description, it is known that the sampler units 1 are arranged in a straight line and separated with each other, thus, no water exchange between two sampling units 1 is permitted and therefore the sampler can be used in sampling the organic pollutants dissolved in the sediment pore water at different depths at a same position. Furthermore, as the heights of the sampling units 1 as well as the clearances between two sampling units 1 may be various, users can configure the sampling units according to the actually required time resolution for more accurate results.

Figure 2:
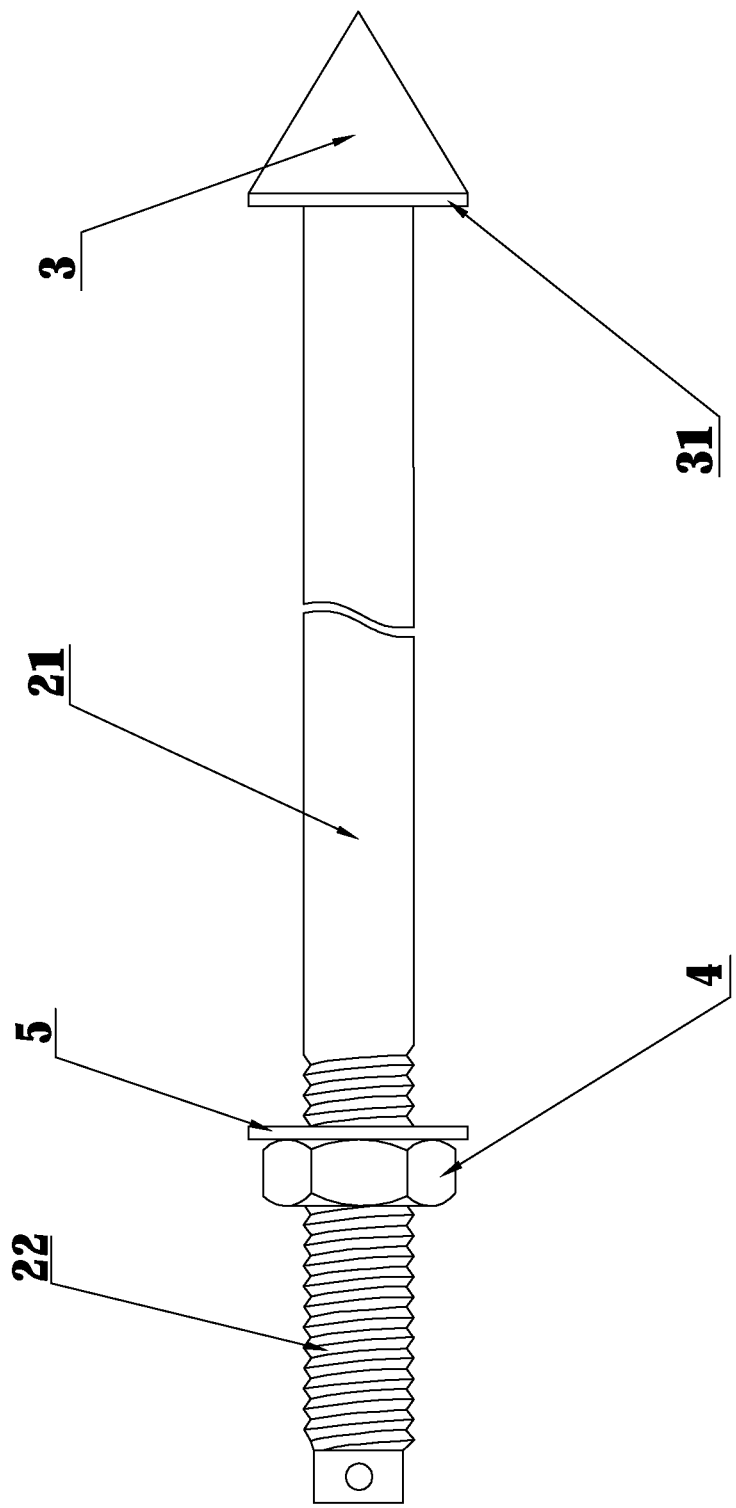
FIG. 2 is a schematic view of the main spindle with fixing elements in FIG. 2.

As a preferred embodiment for the present invention, as shown by FIG. 2, the sampling units 1 are fixed in order through a main spindle 2, the main spindle 2 has a pyramid 3 on one end thereof, a shaft 21 on the middle thereof and a threaded rod 22 on the other end thereof, wherein the pyramid 3 has a stopping tray 31 on the top thereof. Correspondingly, the sampler further comprises a ring 5 and a locking nut 4 mounted on the threaded rod 22 for securing the sampling unites 1 mounted.

In assembly the sampling units 1 are one by one sheathed on the shaft 21 of the main spindle 2 in series, the ring 5 and locking nut 4 is then screwed on the threaded rod 22, thus the sampling units 1 are so fixed between the stopping tray 31 and the tightened locking nut 4. In use the arrangement described above can prevent the sampler from rotation by water flow when the sampler is stabbed into the settled layer through the pyramid 3.

Figure 3:
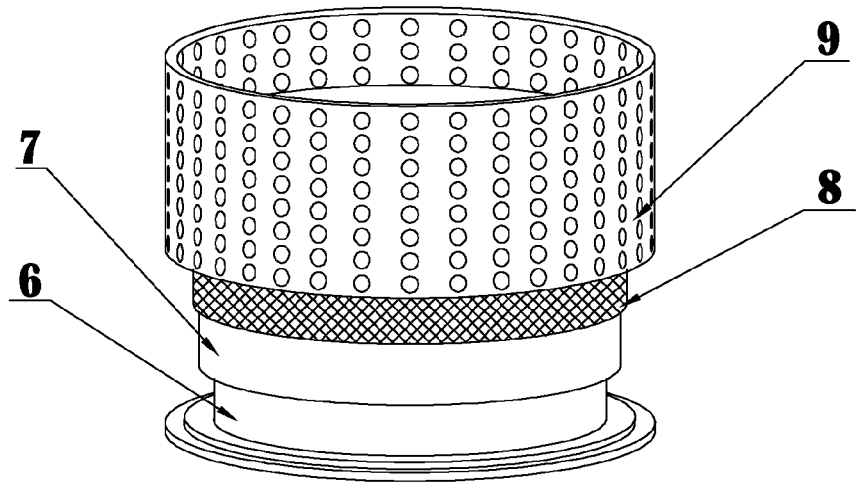
FIG. 3 is a schematic view of the sampling unit in FIG. 1.
Figure 4:
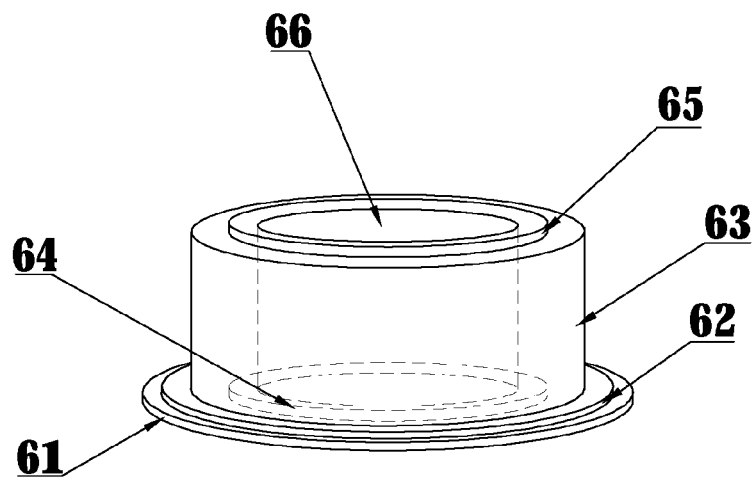
FIG. 4 is a schematic view of the center ring of the sampling unit in FIG. 3.

As shown by FIGS. 3 and 4, in the preferred embodiment, within a sampling unit 1, the adsorption film 7, the filtering membrane 8 and the porous protection pipe 9 are sheathed on the center ring 6 from inside to outside. The center ring 6 has a separation tray 61, a pipe protection tray 62, a column 63, a positioning groove 64 on the side thereof where the unit separation tray 61 is located, and a positioning ring 65 on the other side thereof engaged with the positioning groove 64 of an adjacent sampling unit, the center ring 6 further has a nozzle 66 in the center thereof The porous protection pipe 9 is secured on the center ring 6 through the pipe protection tray 62, said porous protection pipe 9 is provided with a plurality of small through holes used for filtering the large particles and protecting the filtering membrane 8 as well, thereby ensuring only water can go into the sampling units 1.

Each sampling unit 1 is sheathed on the main spindle 2 in series through the nozzle 66 in the center of the center ring 6; the positioning ring 65 of one sampling unit 1 is spliced into the positioning groove 64 of an adjacent sampling unit 1, thereby effectively preventing the relative displacement between two adjacent sampling units 2. The unit separation tray 61 on the center ring 6 can effectively eliminate the possibility of water exchange between two adjacent sampling units 1, so as to improve the time resolutions for the pore water sampling.

The adsorption film 7 is adhered to the outer wall of the column 63, and the filtering membrane 8 is adhered on the adsorption film 7.

In addition, as a preferred embodiment, the pyramid 3 is a square pyramid.

While the invention has been described in terms of what are presently considered to be the most practical and preferred embodiments, it is to be understood that the invention need not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A multi-section sediment pore water sampler, comprising a plurality of sampling units arranged along the axis thereof in a straight line and separated with each other, a main spindle having one and other ends and including a threaded rod for supporting the sampling units, a pyramid mounted at the one end of the main spindle to enable the main spindle to be stabbed into a layer, the pyramid having a stopping tray, said threaded rod extending to the other end of the main spindle, and a locking nut mounted at the other end of the main spindle on the threaded rod for securing the sampling units between the stopping tray and nut, wherein the sampling units are mounted in order on the main spindle and further comprising a ring disposed adjacent to the locking nut mounted on the threaded rod wherein each sampling unit comprises a center ring which is sheathed by an adsorption film, a filtering membrane and a porous protection pipe from inside to outside, the center ring being provided with a separation tray, a pipe protection tray, a column, a positioning groove in the column on the side of the separation tray, a positioning ring on the opposite side of the column matched with the positioning groove of an adjacent sampling unit, and a nozzle therein.

2. The sampler according to claim 1, wherein the pyramid is a square pyramid.

3. A multi-section sediment pore water sampler, comprising a plurality of sampling units arranged along the axis thereof in a straight line and separated with each other, a main spindle having one and other ends and including a threaded rod for supporting the sampling units, a pyramid mounted at the one end of the main spindle to enable the main spindle to be stabbed into a layer, the pyramid having a stopping tray, said threaded rod extending to the other end of the main spindle, and a locking nut mounted at the other end of the main spindle on the threaded rod for securing the sampling units between the stopping tray and nut, wherein each sampling unit comprises a center ring, and an adsorption film that is coaxially disposed about the center ring.

4. The sampler according to claim 3 including a filtering membrane that is coaxially disposed about the adsorption film.

5. The sampler according to claim 4 including a porous protection pipe that is coaxially disposed about the filtering membrane.

6. The sampler according to claim 3 wherein the center ring of each sampling unit is provided with a separation tray and a column.

7. The sampler according to claim 6 including a pipe protection tray, a positioning groove in the column on the side of the separation tray, and a positioning ring on the opposite side of the column matched with the positioning groove of an adjacent sampling unit.

8. A multi-section sediment pore water sampler, comprising a plurality of sampling units arranged along a longitudinal axis, and a mounting spindle for receiving the plurality of sampling units, each sampling unit comprises a center ring arranged about the mounting spindle and which is sheathed by an adsorption film, a filtering membrane and a porous protection pipe from inside to outside.

9. The sampler according to claim 8 wherein the center ring includes a separation tray, a pipe protection tray, and a column.

10. The sampler according to claim 9 including a positioning groove in the column on the side of the separation tray, and a positioning ring on the opposite side of the column.

11. The sampler according to claim 10 wherein the positioning ring is matched with the positioning groove of an adjacent sampling unit.

12. The sampler according to claim 11 wherein the mounting spindle has one and other ends and including a threaded rod for supporting the sampling units.

13. The sampler according to claim 12 including a pyramid mounted at the one end of the main spindle to enable the main spindle to be stabbed into a layer.

14. The sampler according to claim 13 wherein the pyramid has a stopping tray, said threaded rod extending to the other end of the main spindle, and a locking nut mounted at the other end of the main spindle on the threaded rod for securing the sampling units between the stopping tray and nut.

15. The sampler according to claim 14 further comprising a securing ring disposed adjacent to the locking nut mounted on the threaded rod.

16. The sampler according to claim 15 wherein the sampling units are secured between the securing ring on the threaded rod and the pyramid stopping tray.

17. The sampler according to claim 16 wherein the pyramid is a square pyramid.

* * * * *